United States Patent

Cathro et al.

[11] Patent Number: 6,080,157
[45] Date of Patent: Jun. 27, 2000

[54] DEVICE TO STABILIZE THE LAMINA

[75] Inventors: Richard Andrew Cathro; Grant Randall Gillett, both of Dunedin, New Zealand

[73] Assignee: CG Surgical Limited, Dunedin, New Zealand

[21] Appl. No.: 09/043,235

[22] PCT Filed: Sep. 11, 1996

[86] PCT No.: PCT/NZ96/00096

§ 371 Date: Sep. 25, 1998

§ 102(e) Date: Sep. 25, 1998

[87] PCT Pub. No.: WO97/09940

PCT Pub. Date: Mar. 20, 1997

[30] Foreign Application Priority Data

Sep. 12, 1995 [NZ] New Zealand ............................ 272994

[51] Int. Cl.[7] .......................... A61B 17/56; A61B 17/58; A61F 2/30
[52] U.S. Cl. ................................................. 606/61; 606/63
[58] Field of Search .................. 606/61, 62, 63, 606/60; 623/17

[56] References Cited

U.S. PATENT DOCUMENTS

| 4,604,995 | 8/1986 | Stephens et al. | 128/69 |
| 4,611,582 | 9/1986 | Duff | 128/69 |
| 5,147,404 | 9/1992 | Downey | 623/17 |
| 5,282,863 | 2/1994 | Burton | 606/61 |
| 5,304,178 | 4/1994 | Stahurski | 606/61 |
| 5,413,576 | 5/1995 | Rivard | 606/61 |
| 5,496,318 | 3/1996 | Howland et al. | 606/61 |

FOREIGN PATENT DOCUMENTS 7693094  3/1995  Australia ................. A61B 17/58

OTHER PUBLICATIONS

Derwent Abstract Accession No. 85–005046/01, Class P31, SU, A, 1091916 (Moscow Medical Institute) May 15, 1984.
Form PCT/ISA/210, International Search Report, dated Feb. 10, 1998 for PCT/NZ96/00096, International Filing Date Sep. 11, 1993.

*Primary Examiner*—Michael Buiz
*Assistant Examiner*—Vy Q. Bui
*Attorney, Agent, or Firm*—Moore & Van Allen, PLC; Michael G. Johnston

[57] ABSTRACT

A device for dynamically stabilizing the lamina after a laminoplasty includes spacer which is shaped to engage between the severed edges of the lamina. The device also includes a retainer attached to the spacer which is adapted to maintain the spacer in an operative position. A method of dynamically stabilizing the lamina after a laminoplasty is also provided, which includes the steps of positioning the spacer between the severed edges of the lamina, and positioning the retainer to maintain the spacer in the operative position.

15 Claims, 1 Drawing Sheet

DEVICE TO STABILIZE THE LAMINA

This invention relates to a device that dynamically stabilises the lamina after a laminoplasty.

BACKGROUND

Cervical spinal stenosis is a condition in which the opening for the spinal cord that runs through the vertebrae of the spinal column is not quite wide enough to comfortably accommodate the spinal cord. The result is that when the ligaments thicken or there is some bulging of the cervical discs (a natural product of wear and tear through life) the person who is affected begins to experience pressure on their spinal cord. This causes three types of symptoms:

1. It causes pain in the head, neck and arms;
2. It causes weakness and/or numbness and tingling in the arms;
3. It causes clumsiness in the arms and legs.

As a result of these symptoms, some people find that their mobility and their ability to undertake a normal day's work is severely affected. The obvious solution is to make more room for the spinal cord so that the pressure will not happen. There are two methods of creating more room in the cervical spinal canal. The first is a laminectomy in which the bony structures forming the back of the canal and the associated ligaments are removed. This can lead to the swan neck deformity so that although it is a very safe operation and usually quite effective it can result in swan neck deformity which is a very difficult problem to correct and which itself causes a lot of discomfort in the neck and shoulders. This is due to the lack of the supporting structures at the back of the vertebrae which normally perform some of the work of keeping the neck in the right shape.

The alternative and increasingly popular way of doing the operation is called a laminoplasty. In this operation the back of the spine is exposed but instead of the bony structures being removed, they are altered in shape. When the bone has been weakened it is bent outwards opening the canal and providing more room for the spinal cord. The traditional problem has always been to stabilise the lamina in this new position.

One way of stabilising the lamina is to take a bone graft from the hip in the form of a rectangular plate of bone and wedge it in position to try and hold the lamina in its new, more open shape. This is generally effective but because it is not a firm arrangement can lead to some slippage and recurrent narrowing of the spinal canal. It also involves making a separate wound in the area of the hip and taking a bone graft.

It is an object of the present invention to provide a prosthesis device to dynamically stabilise the lamina after laminoplasty.

PRESENT INVENTION

Accordingly the invention consists in a device for dynamically stabilising the lamina of the spine after a laminoplasty comprising spacing means shaped to engage between the severed edges of the lamina and retaining means attached to said spacing means and shaped to maintain the spacing means in an operable position.

This invention also consists in a method of dynamically stabilising reshaped lamina after a laminoplasty comprising the steps of positioning a spacing means between the severed edges of the lamina and positioning a retaining means attached to said spacing means to maintain the spacing means in an operable position.

The invention consists in the foregoing and also envisages constructions of which the following gives examples only.

DRAWING DESCRIPTION

One preferred form of the invention will now be described with reference to the accompanying drawings, in which.

PREFERRED EMBODIMENT

Figure 1:
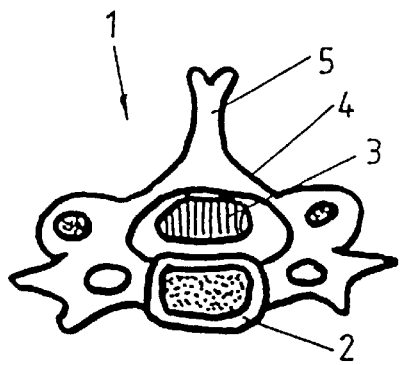
FIG. 1 is a cross section through the back bone.
Figure 2:
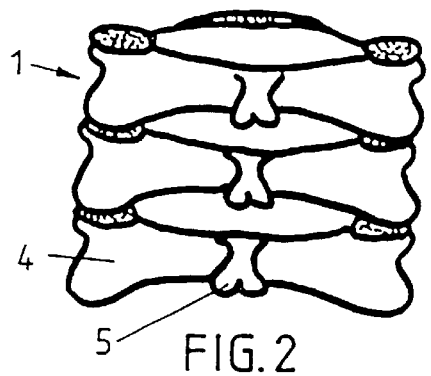
FIG. 2 is a rear view of a section of the back bone.
Figure 4:
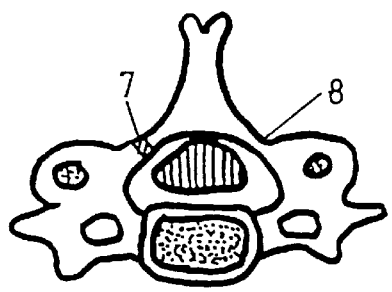
FIG. 4 is a cross section of the back bone illustrating the modifications made in a laminoplasty.

FIGS. 1 and 2 illustrate a section through a joint in the back bone 1 with the vertebrae body 2, spinal cord 3, lamina 4 and spine 5. FIG. 2 shows a rear view of a number of vertebrae.

In a laminoplasty a cut 7 is made through the lamina on one side and a weakening groove 8 is formed on the other side. This weakens the bone so that it can be deformed to a position as illustrated in FIG. 5, but it is necessary to stabilise the deformed lamina.

Figure 5:
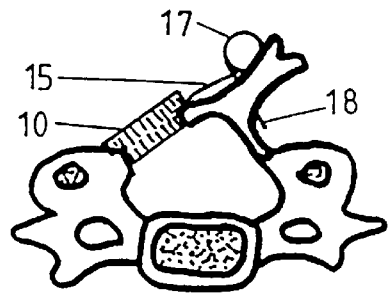
FIG. 5 shows the modified back bone with the device according to the present invention in place.
Figure 3:
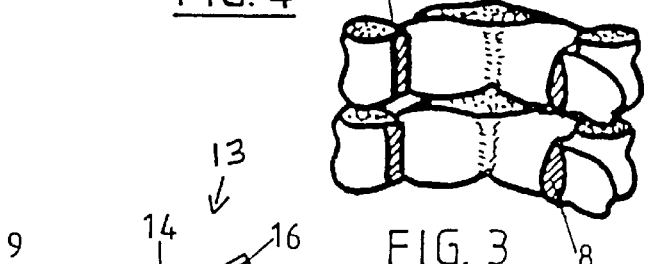
FIG. 3 is a section of the back bone with modifications made.
Figure 6:
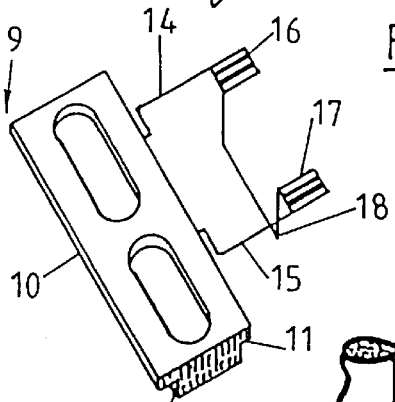
FIG. 6 is a perspective view of a device according to the present invention.
Figure 7:
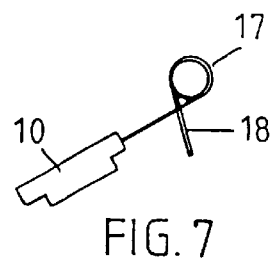
FIG. 7 is an elevation of the device according to the present invention.
Figure 8:
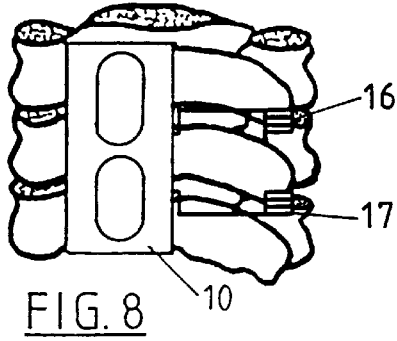
FIG. 8 shows a back view with the device fitted in place.

The present invention provides a stabilising device 9 illustrated in FIGS. 6 and 7 of the accompanying drawings and shown as fitted in place in FIGS. 5 and 8 of the accompanying drawings. It operates in a way that is effective but does not rely on rigid fixation. The device is a substantially rectangular plate 10 having shouldered longitudinal edges 11 and 12. The device can be made from stainless steel or any other suitable material which will not be rejected by the body. It is proposed to make the device from nylon, teflon and/or titanium which will be compatible with the MRI scans should such scans need to be done following surgery.

It is necessary to ensure that the plate 10 is correctly located in place in a way which will avoid or minimise any movement and for this to be achieved simply and effectively in a time efficient way. We have found that the locating device is best achieved by a spring 13 attached with two arms 14 and 15 extending from the rectangular plate formed into a spring coil 16 and 17 on each side and then continued as a U shaped section 18 joining or completing the spring clip with the U shape section 18 in use located behind the spine 5 as is particularly illustrated in FIG. 5 with the springs 16 and 17 fitting between the vertebrae as illustrated particularly in FIG. 8.

As a consequence of the present invention it has been possible to reduce the operating time by half and to lessen the theoretical likelihood of recurrent narrowing of the spine. Another significant advantage for the patient is a more comfortable resulting neck that is achieved using other known procedures. As a consequential advantage over the need for removing a bone graft from the hip, the patient will have no discomfort in the hip which is often the most painful part of the traditional laminoplasty method.

The technique applied in fitting the device uses known means to encourage fusion between the device and the cut lamina, for example, by placing bone chips obtained from the neck during the laminoplasty around the device. However, it must be appreciated that any spinal operation carries a risk and while we have been very confident that the present invention will offer an advantage and will not carry any greater risk than other posterior approach to the cervical spine, the design of the present device has been adopted to minimise or eliminate slippage of the device once its fitted and to function so that it will retain the enlarged spinal canal. It is considered that the present invention and the technique of applying the device represents a significant improvement in an area which is medically recognised as requiring particular care because of the consequences that follow from damaging the spinal cord.

We claim:

1. A surgical implant device for dynamically stabilizing the lamina of the spine after a laminoplasty comprising:

a spacing means having opposed edges, the edges being appropriately spaced for engagement, in an operative position, with the severed edges of the lamina, with each edge of the spacing means shaped to engage with a respective severed edge of the lamina; and a retaining means attached to said spacing means and adapted to maintain the spacing means in the operative position.

2. A surgical implant device as claimed in claim 1 wherein said spacing means comprises a plate of substantially rectangular configuration.

3. A surgical implant device as claimed in claim 1 wherein said device is made from nylon.

4. A surgical implant device as claimed in claim 1 wherein said device is made from Teflon.

5. A surgical implant device as claimed in claim 1 wherein said device is made from titanium.

6. A surgical implant device as claimed in claim 1 wherein the spacing means is substantially planar and the opposed edges of the spacing means are substantially T-shaped in cross-section, the intersection of the cross member and shank of the "T" defining a notch for engaging the respective severed edges of the lamina.

7. A surgical implant device as claimed in claim 1 wherein the shape of the opposed edges of the spacing means defines a notch for engaging a respective severed edge of the lamina.

8. A surgical implant device as claimed in claim 1 wherein said retaining means comprises a spring clip.

9. A surgical implant device as claimed in claim 8, wherein the spring clip comprises:

two arms extending from the spacing means;
   a U-shaped section to engage around the spine; and
   spring means between the arms and the U-shaped section.

10. A device for dynamically stabilizing the lamina of the spine after a laminoplasty comprising:

spacing means shaped to engage between the severed edges of the lamina; and retaining means attached to said spacing means and shaped to maintain the spacing means in an operable position, wherein said retaining means comprises a spring clip having:
    two arms extending from the spacing means;
    a U-shaped section to engage over the spine; and
    spring means between the arms and the U-shaped section.

11. A method of dynamically stabilizing reshaped lamina after a laminoplasty comprising the steps of:

providing a spacing means having opposed edges, the edges of the spacing means shaped to engage with a respective severed edge of the lamina, and a retaining means attached to said spacing means, positioning the spacing means between the severed edges of the lamina so that the opposed edges of the spacing means engage with a respective severed edge of the lamina; and positioning the retaining means to maintain the spacing means in the operative position.

12. A method of/dynamically stabilising reshaped lamina after a laminoplasty as claimed in claim 11 wherein said retaining means is positioned to engage over the spine.

13. A method as claimed in claim 11 wherein each edge of the spacing means has a notch to engage with a respective severed edge of the lamina.

14. A method as claimed in claim 11 wherein said retaining means comprises a spring clip.

15. A method as claimed in claim 14 wherein the spring clip comprises:

two arms extending from the spacing means;
    a U-shaped section to engage around the spine; and
    spring means between the arms and the U-shaped section.

* * * * *